(12) United States Patent
Deacon

(10) Patent No.: US 8,897,629 B1
(45) Date of Patent: Nov. 25, 2014

(54) SCENT DELIVERY APPARATUS

(75) Inventor: David Deacon, Los Altos, CA (US)

(73) Assignee: Scent Sciences Corporation, San Jose, CA (US)

( * ) Notice: Subject to any disclaimer, the term of this patent is extended or adjusted under 35 U.S.C. 154(b) by 330 days.

(21) Appl. No.: 13/360,402

(22) Filed: Jan. 27, 2012

(51) Int. Cl.
*B05B 1/24* (2006.01)
*B05B 17/04* (2006.01)
*A61L 9/03* (2006.01)
*H05B 3/44* (2006.01)

(52) U.S. Cl.
USPC .............. 392/394; 392/403; 239/86; 239/136

(58) Field of Classification Search
None
See application file for complete search history.

(56) References Cited

U.S. PATENT DOCUMENTS

| | | | | |
|---|---|---|---|---|
| 3,891,826 A * | 6/1975 | Seuthe et al. | ................. | 392/405 |
| 3,944,777 A | 3/1976 | Porat | ............................ | 219/118 |
| 4,419,302 A * | 12/1983 | Nishino et al. | ................. | 261/142 |
| 5,047,790 A | 9/1991 | Cowger et al. | ............ | 346/140 R |
| 5,683,246 A | 11/1997 | Coss et al. | ...................... | 433/29 |
| 5,949,522 A | 9/1999 | Manne | ............................ | 352/85 |
| 6,137,084 A | 10/2000 | Thomas | ........................ | 219/202 |
| 6,149,873 A | 11/2000 | Potter et al. | ..................... | 422/123 |
| 6,169,595 B1 | 1/2001 | Manne | ............................ | 352/85 |
| 6,293,474 B1 | 9/2001 | Helf et al. | .................. | 239/102.2 |
| 6,371,451 B1 | 4/2002 | Choi | ................................ | 261/26 |
| 6,417,623 B1 | 7/2002 | Chamberlain et al. | .......... | 315/82 |
| 6,565,198 B2 | 5/2003 | Saruta et al. | ..................... | 347/86 |
| 6,592,104 B2 | 7/2003 | Cox | ................................ | 261/26 |
| 6,640,050 B2 * | 10/2003 | Nichols et al. | ................ | 392/390 |
| 6,713,024 B1 | 3/2004 | Arnell et al. | ................... | 422/124 |
| 6,744,488 B2 | 6/2004 | Schermerhorn | ................ | 352/85 |
| 6,783,117 B2 | 8/2004 | Wohrle | ............................ | 261/26 |
| 6,943,327 B2 | 9/2005 | Fabregas et al. | ............... | 219/494 |
| 7,093,927 B2 | 8/2006 | Tsuji | ............................... | 347/50 |
| 7,100,841 B2 * | 9/2006 | Ivey et al. | ...................... | 239/136 |
| 7,154,579 B2 | 12/2006 | Selander et al. | ................ | 352/85 |
| 7,188,783 B2 * | 3/2007 | Ivey et al. | ...................... | 239/136 |
| 7,212,637 B2 | 5/2007 | Salisbury | ....................... | 380/270 |
| 7,225,998 B2 * | 6/2007 | Pellizzari | ....................... | 239/136 |
| 7,249,833 B2 | 7/2007 | Silverbrook et al. | ............ | 347/86 |
| 7,344,214 B2 | 3/2008 | Chan | ................................. | 347/7 |
| 7,365,874 B2 | 4/2008 | Lapstun et al. | ................ | 358/1.3 |
| 7,372,210 B2 | 5/2008 | Scolaro et al. | ............ | 315/209 R |
| 7,431,570 B2 | 10/2008 | Young et al. | ................... | 417/208 |
| 7,437,061 B2 | 10/2008 | Manne | ........................... | 392/390 |
| 7,490,833 B2 * | 2/2009 | Harris et al. | .................... | 273/243 |
| 7,718,119 B2 | 5/2010 | Tajima et al. | ...................... | 422/5 |
| 7,755,303 B2 | 7/2010 | Johnson et al. | ............... | 315/308 |
| 7,893,624 B2 | 2/2011 | Huang | ........................... | 315/112 |
| 7,920,777 B2 * | 4/2011 | Rabin et al. | ................... | 392/396 |
| 7,942,644 B2 | 5/2011 | Young et al. | ................... | 417/208 |
| 8,442,390 B2 * | 5/2013 | Nichols et al. | ................ | 392/403 |

(Continued)

*Primary Examiner* — Joseph M Pelham
(74) *Attorney, Agent, or Firm* — Pillsbury Winthrop Shaw Pittman LLP

(57) ABSTRACT

A filament may be provided having enhanced solderability and/or heating characteristics configured for heating a substance to release an airborne scent. In exemplary implementations, the ends of a high-temperature compatible filament may be coated with a metal film having greater solderability and/or conductivity relative to the filament. The coated ends may allow the filament to be incorporated into a heating circuit using low-temperature solder, rather than by using high-temperature solder or clamping. The coated ends may have a lower resistance relative to uncoated portions of the filament such that, when electrical current is passed through the filament, most of the current will flow through the coating at the end portions of the filament concentrating heat emitted by the filament to the uncoated portions.

13 Claims, 3 Drawing Sheets

(56) References Cited

U.S. PATENT DOCUMENTS

Figure 1:
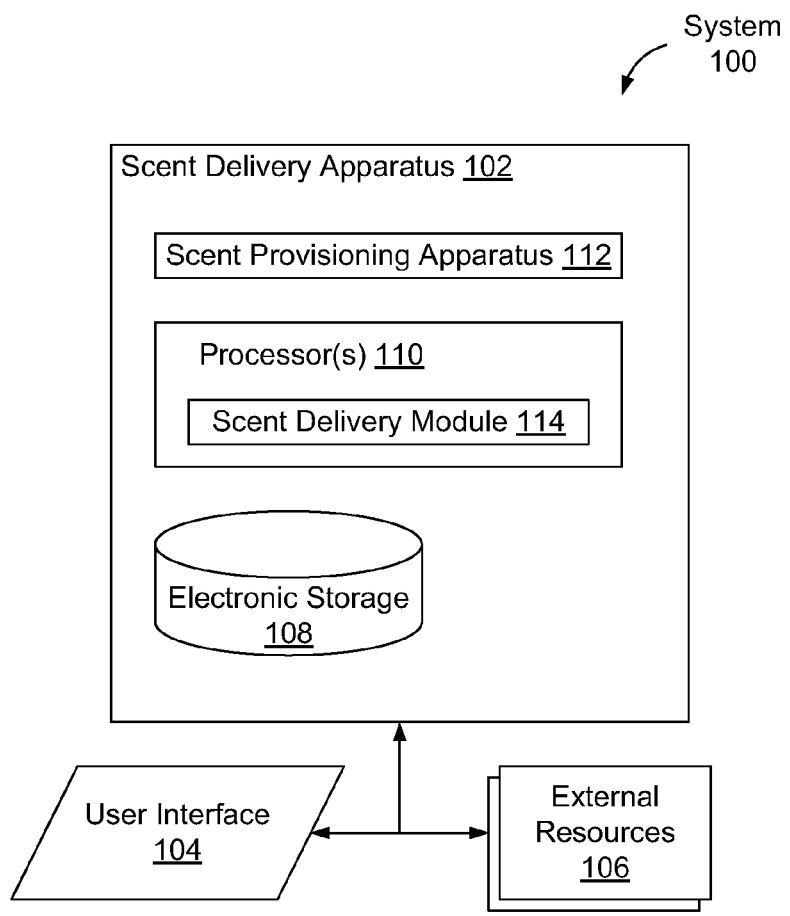

| | | | |
|---|---|---|---|
| 8,454,417 B2* | 6/2013 | Harris et al. | 463/7 |
| 2003/0006302 A1* | 1/2003 | Ivey et al. | 239/135 |
| 2003/0006303 A1* | 1/2003 | Ivey et al. | 239/136 |
| 2003/0206834 A1 | 11/2003 | Chiao et al. | 422/124 |
| 2006/0018787 A1 | 1/2006 | Guo | 422/5 |
| 2007/0023540 A1* | 2/2007 | Selander | 239/34 |
| 2009/0220222 A1* | 9/2009 | Rabin et al. | 392/396 |
| 2012/0230659 A1* | 9/2012 | Goodman et al. | 392/395 |
| 2013/0199528 A1* | 8/2013 | Goodman et al. | 128/203.26 |

* cited by examiner

SCENT DELIVERY APPARATUS

FIELD OF THE DISCLOSURE

The invention relates to a filament having enhanced solderability and/or heating characteristics configured for heating a substance to release an airborne scent, systems and methods utilizing the filament, and methods for fabricating the filament.

BACKGROUND

Heating substances in order to release an airborne scent is known. Some existing approaches utilize a high-temperature filament to heat the substance. These filaments, however, typically do not wet low-temperature solders. As such, existing filaments may require clamping or high-temperature solder to be incorporated into a heating circuit. Clamping may lead to inconsistent electrical connections and/or bulkiness of a system comprising such a filament. High-temperature solder may damage adjacent components and/or the filament itself during application. Additionally, existing filaments generally heat along the full length of the filament, making it difficult to heat targeted areas.

SUMMARY

One aspect of the invention may relate to coating the ends of a high-temperature compatible filament with a metal film having greater solderability and/or conductivity relative to the filament. The coated ends may allow the filament to be soldered using low-temperature solder. The coated ends may have a lower resistance relative to uncoated portions of the filament such that, when electrical current is passed through the filament, most of the current will flow through the coating at the end portions of the filament concentrating heat emitted by the filament to the uncoated portions.

Another aspect of the invention relates to a system configured to provide one or more airborne scents in an environment of a user. The system may include a scent delivery apparatus, a user interface, external resources, and/or other components.

The scent delivery apparatus may be configured to emit one or more airborne scents in an environment of a user. Emission of the one or more scents may be coordinated with presentation of various media, in some implementations. Such media may include a video, a video game, a still picture, audio, text, and/or other media. Emission of the one or more scents may correspond to subject matter of media being presented. By way of non-limiting example, a rose scent may be emitted when a field of roses is shown in the movie.

The user interface may be configured to provide an interface between system and users. The user interface may include one or more devices suitable for introducing a scent in an environment of a user. Examples of such devices may include a nasal mask, total face mask, nasal cannula, and/or other devices suitable for introducing a scent in an environment of a user.

The external resources may be configured to provide media for presentation to a user. By way of non-limiting example, external resources may include one or more of an entertainment center, gaming console, computing platform, digital device, television, movie projector, stereo, digital picture presentation device, e-book reader, and/or other resources configured to provide media for presentation to a user.

Referring again to scent delivery apparatus, it may include electronic storage, one or more processors, a scent provisioning apparatus, and/or other components. The processor(s) may be configured to execute one or more computer program modules. In some implementations, the one or more computer program modules may include a scent delivery module and/or other modules.

The scent delivery module may be configured to control emission of one or more scents by the scent provisioning apparatus, which is described in further detail herein. Emission of the one or more scents may be controlled based on media being presented to a user, information received from external resources and/or other components of the system, information received from a user via the user interface, and/or other information. In some implementations, scent delivery module may control emission by controlling a level of current passed through a filament and/or other heating element configured to heat a substance that emits a scent when heated.

The scent provisioning apparatus may include a reservoir, a capillary, a filament, and/or other components. In some implementations, one or more scent provisioning apparatuses may be included in a cartridge configured to be removably coupled with scent delivery apparatus.

The reservoir may be configured to contain a substance. The substance may be configured to release an airborne scent responsive to being heated. According to various implementations, substance may include an oil and/or other liquid, a gel, and/or other substances configured to release an airborne scent responsive to being heated.

The capillary may include a tube with a fine bore. The capillary may be disposed at least partially within the reservoir. The capillary may be configured to draw the substance through a portion of the capillary by way of capillary action. Capillary action, or capillarity, may be an ability of a liquid or other viscous substance to flow against gravity where the liquid spontaneously rises in a tube with a fine bore.

The filament may be a wire or strand of a high-temperature compatible conductive material. By way of non-limiting example, the filament may be formed at least partially of an alloy comprising nickel and chromium (e.g., nichrome). The filament may be disposed at least partially within the capillary. The filament may be configured to heat the substance within the capillary by way of resistive heating. Resistive heating may be provided by passing a current through the filament. According to some implementations, an intensity of the airborne scent released responsive to heating the substance may be controlled based on the temperature level of the filament.

Two or more portions of the filament may have a coating thereon. The coating may include a material having higher conductivity relative to the filament, which may reduce resistive heating of the two or more portions of the filament where the coating is disposed relative to an uncoated segment of the filament. As a result, non-coated portions of the filament may emit greater levels of heat energy than coated portions under the same amount of current. This may facilitate the delivery of heat to one or more specific regions within the capillary.

The coating may include a material having better solderability relative to filament. Thus, the coating may enhance solderability of the two or more portions of the filament where the coating is disposed relative to an uncoated segment of the filament. As such, low-temperature solder may be used to incorporate filament into a heating circuit.

Yet other aspects of the invention relate to methods for preparing and/or utilizing a filament configured to heat a liquid in order to release an airborne scent, as well as to such a filament itself. At one operation, a filament may be coated at least partially with copper or an alloy comprising copper to form a coating on two or more portions of the filament. At another operation, at least a portion of the copper or copper alloy coating may be coated with an outer layer of tin. At still another operation, at least one portion of the filament may be coiled. At yet another operation, the filament may be disposed at least partially within the capillary. At a further operation, the capillary and filament assembly may be disposed at least partially within a reservoir configured to contain a substance, which may release the airborne scent responsive to being heated. At a still further operation, current may be passed through the filament to heat the substance within the capillary by way of resistive heating. At a yet further operation, an airborne scent is released responsive to the substance within the capillary being heated.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of “a”, “an”, and “the” include plural referents unless the context clearly dictates otherwise.

BRIEF DESCRIPTION OF THE DRAWINGS

FIG. 1 illustrates a system configured to provide one or more airborne scents in an environment of a user, in accordance with one or more implementations.

FIG. 2 illustrates a scent provisioning apparatus included in the system of FIG. 1, in accordance with one or more implementations.

FIG. 3 illustrates a method for preparing and/or utilizing a filament configured to heat a liquid in order to release an airborne scent, in accordance with one or more implementations.

DETAILED DESCRIPTION

FIG. 1 illustrates a system 100 configured to provide one or more airborne scents in an environment of a user, in accordance with one or more implementations. As depicted in FIG. 1, system 100 may include a scent delivery apparatus 102, a user interface 104, external resources 106, and/or other components. The depiction of system 100 in FIG. 1 is not intended to be limiting as system 100 may include more or less components than those shown. Additionally, two or more components of system 100 may be combined as singular components.

The scent delivery apparatus 102 may be configured to emit one or more airborne scents in an environment of a user. Emission of the one or more scents may be coordinated with presentation of various media, in some implementations. Such media may include a video, a video game, a still picture, audio, text, and/or other media. Emission of the one or more scents may correspond to subject matter of media being presented. By way of non-limiting example, emission of a given scent during presentation of a movie may correspond to subject matter being presently being shown in the movie, such as a rose scent being emitted when a field of roses is shown in the movie. The scent delivery apparatus 102 and components thereof are described in further detail herein.

The user interface 104 may be configured to provide an interface between system 100 and users. The user interface 104 may include one or more devices suitable for introducing a scent in an environment of a user. Examples of such devices may include a nasal mask, total face mask, nasal cannula, and/or other devices suitable for introducing a scent in an environment of a user. The user interface 104 may also include a headgear assembly, such as mounting straps or a harness, for removing and fastening user interface 104 to a user. In some implementations, user interface 104 may have controls and/or a position sensor mounted thereon. In short, any technique for introducing a scent to an environment of a user is contemplated by the present invention as user interface 104.

In accordance with some implementations, the user interface 104 may be further configured to enable data, results, and/or instructions and any other communicable items, collectively referred to as “information,” to be communicated between the users and system 100. Examples of interface devices suitable for inclusion in user interface 104 include a keypad, buttons, switches, a keyboard, knobs, levers, a display screen, a touch screen, speakers, a microphone, an indicator light, an audible alarm, and a printer. It is to be understood that other communication techniques, either hard-wired or wireless, are also contemplated by the present invention as user interface 104. For example, the present invention contemplates that user interface 104 may be integrated with a removable storage interface provided by electronic storage 108. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 104 include, but are not limited to, an RS-232 port, RF link, an IR link, modem (telephone, cable or other). In short, any technique for communicating information with system 100 is contemplated by the present invention as user interface 104.

The external resources 106 may be configured to provide media for presentation to a user. By way of non-limiting example, external resources 106 may include one or more of an entertainment center, gaming console, computing platform, digital device, television, movie projector, stereo, digital picture presentation device, e-book reader, and/or other resources configured to provide media for presentation to a user. The external resources 106 may include sources of information, hosts and/or providers of media content outside of system 100, external entities participating with system 100, and/or other resources. In some implementations, some or all of the functionality attributed herein to external resources 106 may be provided by resources included in system 100.

As depicted in FIG. 1, scent delivery apparatus 102 may include electronic storage 108, one or more processors 110, a scent provisioning apparatus 112, and/or other components. The depiction of scent delivery apparatus 102 in FIG. 1 is not intended to be limiting as scent delivery apparatus 102 may include more or less components than those shown. Additionally, two or more components of scent delivery apparatus 102 may be combined as singular components.

The processor(s) 110 may be configured to execute one or more computer program modules. The processor(s) 110 may be configured to execute the computer program module(s) by software; hardware; firmware; some combination of software, hardware, and/or firmware; and/or other mechanisms for configuring processing capabilities on processor(s) 110. In some implementations, the one or more computer program modules may include a scent delivery module 114 and/or other modules.

The scent delivery module 114 may be configured to control emission of one or more scents by scent provisioning apparatus 112, which is described in further detail in connection with FIG. 2. Emission of the one or more scents may be controlled based on media being presented to a user, information received from external resources 106 and/or other components of system 100, information received from a user via user interface 104, and/or other information. In some implementations, scent delivery module 114 may control emission by controlling a level of current passed through a filament and/or other heating element configured to heat a substance that emits a scent when heated.

Figure 2:
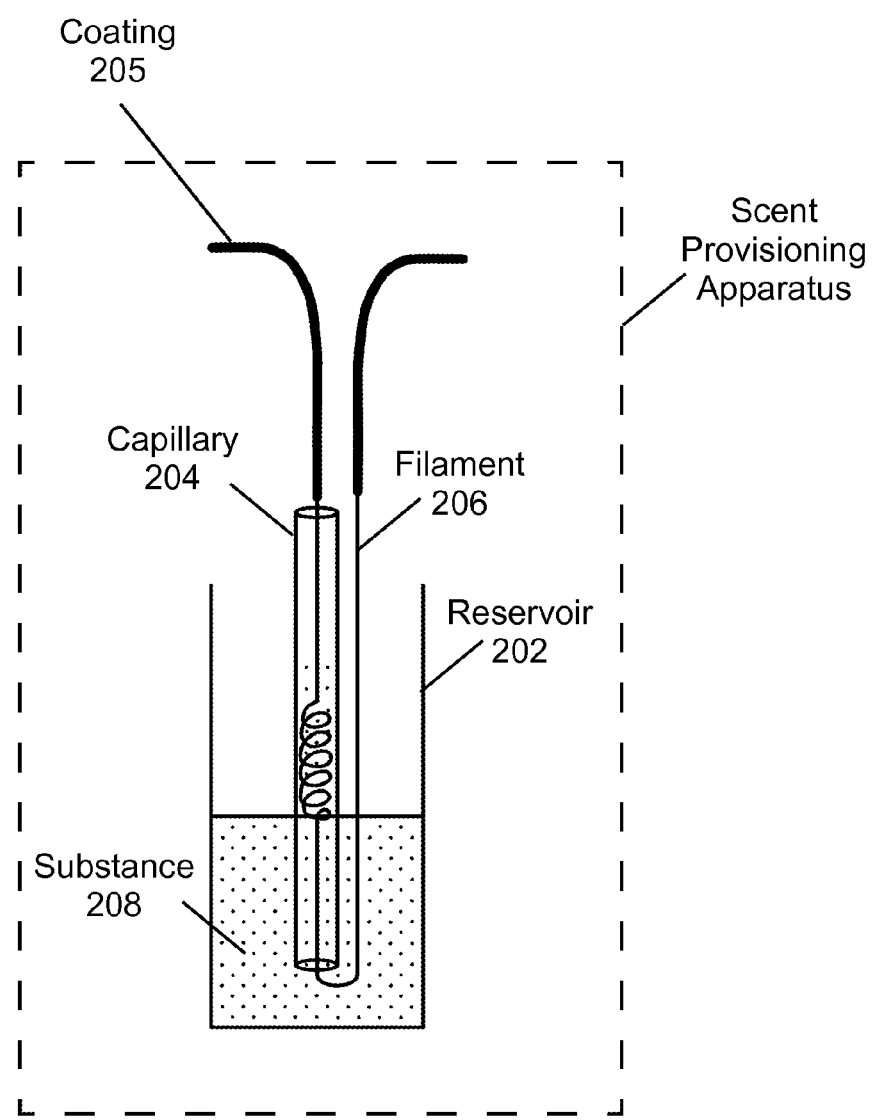

FIG. 2 illustrates scent provisioning apparatus 112, in accordance with one or more implementations. As depicted in FIG. 2, scent provisioning apparatus 112 may include a reservoir 202, a capillary 204, a filament 206, and/or other components. The depiction of scent provisioning apparatus 112 in FIG. 2 is not intended to be limiting as scent provisioning apparatus 112 may include more or less components than those shown. Additionally, two or more components of scent provisioning apparatus 112 may be combined as singular components. In some implementations, one or more scent provisioning apparatuses (e.g., scent provisioning apparatus 112) may be included in a cartridge configured to be removably coupled with scent delivery apparatus 102.

The reservoir 202 may be configured to contain a substance 208. The substance 208 may be configured to release an airborne scent responsive to being heated. According to various implementations, substance 208 may include an oil and/or other liquid, a gel, and/or other substances configured to release an airborne scent responsive to being heated.

The capillary 204 may include a tube with a fine bore. As depicted in FIG. 2, capillary 204 may be disposed at least partially within reservoir 202. The capillary 204 may be open at both ends. The capillary 204 may be configured to draw substance 208 through a portion of capillary 204 by way of capillary action. Capillary action, or capillarity, may be an ability of a liquid or other viscous substance to flow against gravity where the liquid spontaneously rises in a tube with a fine bore.

The filament 206 may be a wire or strand of a high-temperature compatible conductive material. By way of non-limiting example, filament 206 may be formed at least partially of an alloy comprising nickel and chromium (e.g., nichrome). As depicted in FIG. 2, filament 206 may be disposed at least partially within capillary 204. In some implementations, filament 206 may be coiled within capillary 204, such as in a coaxial manner. The filament 206 may be configured to heat substance 208 within capillary 204 by way of resistive heating. Resistive heating may be provided by passing a current through filament 206. The scent delivery module 114 (see FIG. 1) may be configured to control a level of current passing through filament 206, thereby controlling a temperature level of filament 206. According to some implementations, an intensity of the airborne scent released responsive to heating substance 208 may be controlled based on the temperature level of filament 206.

Two or more portions of filament 206 may have a coating (e.g., coating 205) thereon. In exemplary implementations, the two end portions of filament 206 may have the coating there on. The coating may include a material having higher conductivity relative to filament 206, which may reduce resistive heating of the two or more portions of filament 206 where the coating is disposed relative to a segment of filament 206 lacking such a coating. As a result, non-coated portions of filament 206 may emit greater levels of heat energy than coated portions under the same amount of current. This may facilitate the delivery of heat to one or more specific regions within capillary 204.

The coating may include a material having better solderability relative to filament 206. Generally speaking, the solderability of a substrate (e.g., filament 206) may be a measure of the ease with which a soldered joint can be made to that material. Good solderability typically requires wetting (i.e., low contact angle) of the substrate by the solder. Thus, the coating may enhance solderability of the two or more portions of filament 206 where the coating is disposed relative to an uncoated segment of filament 206. As such, low-temperature solder may be used to incorporate filament 206 into a heating circuit.

By way of non-limiting example, the coating may include copper, an alloy comprising copper, and/or other materials having higher conductivity and better solderability relative to filament 206. Copper and some alloys containing copper may have a higher conductivity and/or better solderability relative to nichrome and some other alloys comprising nickel and chromium. In some implementations, a portion of the copper or copper alloy coating may have an outer layer of tin disposed thereon. This may further enhance solderability of the two or more portions of filament 206 where the coating is disposed relative to an uncoated segment of filament 206.

Referring again to FIG. 1, processor(s) 110 may be configured to provide information processing capabilities in system 100. As such, processor(s) 110 may include one or more of a digital processor, an analog processor, a digital circuit designed to process information, an analog circuit designed to process information, a state machine, and/or other mechanisms for electronically processing information. Although processor(s) 110 is shown in FIG. 1 as a single entity, this is for illustrative purposes only. In some implementations, processor(s) 110 may include a plurality of processing units. These processing units may be physically located within the same device, or processor(s) 110 may represent processing functionality of a plurality of devices operating in coordination (e.g., "in the cloud", and/or other virtualized processing solutions).

It should be appreciated that although scent delivery module 114 is illustrated in FIG. 1 as being located within a single processing unit, in implementations in which processor(s) 110 includes multiple processing units, scent delivery module 114 may be located remotely from scent delivery apparatus 102. The description of the functionality provided by scent delivery module 114 described herein is for illustrative purposes, and is not intended to be limiting, as scent delivery module 114 may provide more or less functionality than is described. For example, some or all of the functionality attributed to scent delivery module 114 may be provided by one or more other modules executed by processor(s) 110.

The electronic storage 108 may comprise electronic storage media that stores information. The electronic storage media of electronic storage 108 may include system storage that is provided integrally (i.e., substantially non-removable) with scent delivery apparatus 102 and/or other components of system 100. The electronic storage media of electronic storage 108 may include removable storage that is removably connectable to scent delivery apparatus 102 and/or other components of system 100 via, for example, a port (e.g., a USB port, a firewire port, etc.) or a drive (e.g., a disk drive, etc.). The electronic storage 108 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage 108 may include virtual storage resources, such as storage resources provided via a cloud and/or a virtual private network. The electronic storage 108 may store software algorithms, information determined by system 100, information received via user interface 104, and/or other information that enables system 100 to function as described herein. The electronic storage 108 may be a separate component within system 100, or electronic storage 108 may be provided integrally with one or more other components of system 100 (e.g., processor(s) 110).

Figure 3:
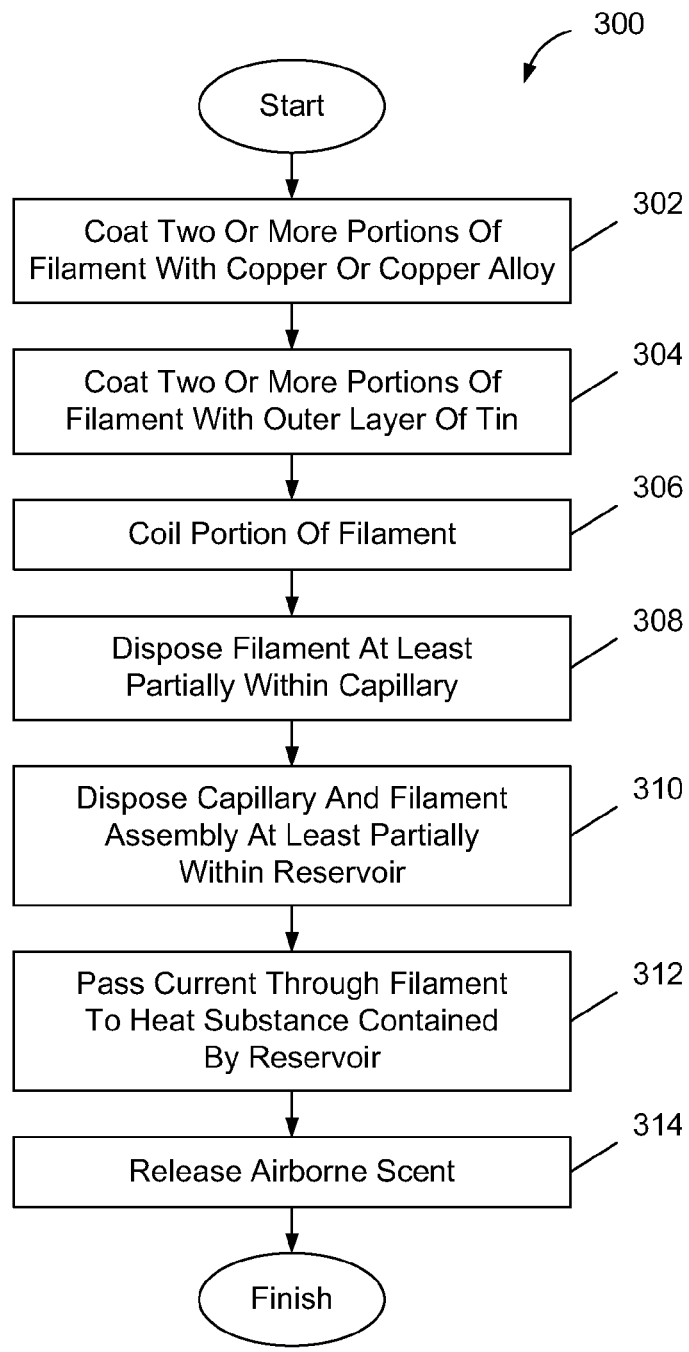

FIG. 3 illustrates a method 300 for preparing and/or utilizing a filament configured to heat a liquid in order to release an airborne scent, in accordance with one or more implementations. The operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not intended to be limiting.

In some implementations, one or more operations of method 300 may be performed by one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At operation 302, a filament (e.g., filament 206) may be coated at least partially with copper or an alloy comprising copper to form a coating on two or more portions of the filament. In some implementations, the two end portions of the filament may be coated with copper or the copper alloy. The coating may be configured to: (1) reduce resistive heating of the two or more portions of the filament where the coating is disposed relative to an uncoated segment of the filament, and/or (2) enhance solderability of the two or more portions of the filament where the coating is disposed relative to an uncoated segment of the filament.

According to some implementations, coating the filament at least partially with copper or the copper alloy to form the coating on the two or more portions of the filament may include: (1) coating some or all of the filament with copper or the copper alloy, (2) etching at least one portion of the coated filament to remove some of the copper or copper alloy in order to form the coating on the two or more portions of the filament, and/or other processing steps.

In some implementations, coating the filament at least partially with copper or the copper alloy to form the coating on the two or more portions of the filament may include: (1) masking at least one portion of the filament, (2) electroplating the filament with copper or the copper alloy, (3) removing the masking from the at least one portion of the filament in order to form the coating on the two or more portions of the filament, and/or other processing steps. Furthermore, coating the filament at least partially with copper or the copper alloy to form the coating on the two or more portions of the filament may include using a reel-to-reel processing technique.

At operation 304, at least a portion of the copper or copper alloy coating may be coated with an outer layer of tin. This may further enhance solderability of the two or more portions of the filament where the coating is disposed relative to an uncoated segment of the filament. Similar or other coating processes as for copper or the copper alloy may be used to apply the outer layer of tin.

At operation 306, at least one portion of the filament may be coiled. The at least one coiled portion of the filament may be configured to be disposed within a capillary (e.g., capillary 204). In some implementations, a middle portion of the filament may be coiled.

At operation 308, the filament may be disposed at least partially within the capillary. In some implementations, one end of the filament may protrude longitudinally from one end of the capillary, which the other end of the filament may be bent back on itself, but outside of the capillary, such the both ends of the filament extend in approximately the same direction (see, e.g., FIG. 2).

At operation 310, the capillary and filament assembly may be disposed at least partially within a reservoir (e.g., reservoir 202) configured to contain a substance (e.g., substance 208). The substance may be configured to release the airborne scent responsive to being heated. The capillary may be configured to draw the substance through a portion of the capillary by way of capillary action.

At operation 312, current may be passed through the filament to heat the substance within the capillary by way of resistive heating. In some implementations, scent delivery module 114 may control controlling a level of current passed through the filament based on media being presented to a user, information received from external resources 106 and/or other components of system 100, information received from a user via user interface 104, and/or other information.

At operation 314, an airborne scent is released responsive to the substance within the capillary being heated. In exemplary implementations, releasing the airborne scent may be coordinated with presentation of various media such that the airborne scent corresponds to subject matter of media being presented. By way of non-limiting example, emission of a given scent during presentation of a digital picture may correspond to subject matter of the digital picture, such as a chocolate scent being emitted when a digital picture is of a chocolate candy.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any implementation can be combined with one or more features of any other implementation.

What is claimed is:

1. A scent delivery apparatus configured to emit one or more airborne scents in an environment of a user, the apparatus comprising:

a scent provisioning apparatus comprising:

a reservoir configured to contain a substance, the substance being configured to release an airborne scent responsive to being heated;

a capillary disposed at least partially within reservoir, the capillary comprising a tube with a bore configured to draw the substance through a portion of the capillary by way of capillary action; and a filament comprising a strand of a high-temperature compatible conductive material, the filament including two end portions having a coating thereon, the coating including a material configured to reduce a resistive heating of the two end portions, at least a non-coated portion of the filament being disposed at least partially within the capillary, the filament being configured to heat the substance within the capillary by way of resistive heating provided by passing a current through the filament, wherein the non-coated portion of the filament emits a greater level of heat than the coated two end portions under the same amount of current, such that the non-coated portion facilitates the delivery of the greater level of heat to one or more specific regions within the capillary where the non-coated portion is at least partially disposed;

wherein the scent delivery apparatus is configured to receive information associated with a level of current to be passed through the filament to control a temperature level of the filament, an intensity of the airborne scent released responsive to heating the substance being controlled based on the temperature level of the filament.

2. The apparatus of claim 1, wherein the scent delivery apparatus is configured to be communicatively coupled with an external device configured to provide media for presentation to the user.

3. The apparatus of claim 2, wherein the external device comprises one or more processors configured to execute a scent delivery module, the scent delivery module being configured to control the level of current passing through the filament to control the temperature level of the filament.

4. The apparatus of claim 2, wherein the external device includes one or more of an entertainment center, a gaming console, a computing platform, a digital device, a television, a movie projector, a stereo, a digital picture presentation device, or an e-book reader.

5. The apparatus of claim 1, wherein an emission of the airborne scent is coordinated with a presentation of media.

6. The apparatus of claim 5, wherein the media includes one or more of a video, a video game, a still picture, audio, or text.

7. The apparatus of claim 5, wherein the emission of the airborne scent corresponds to subject matter of the media being presented.

8. The apparatus of claim 1, wherein the scent provisioning apparatus is configured to be operatively coupled to a user interface configured to introduce a scent in an environment of a user.

9. The apparatus of claim 8, wherein the user interface includes one or more of a nasal mask, a total face mask, or a nasal cannula.

10. The apparatus of claim 8, wherein the user interface includes a headgear assembly having one or both of mounting straps or a harness.

11. The apparatus of claim 1, wherein the substance includes one or both of an oil or a gel.

12. The apparatus of claim 1, wherein the filament is coiled within at least a portion of the capillary.

13. The apparatus of claim 12, wherein the filament is coiled in a coaxial manner.

* * * * *